US010493227B2

(12) United States Patent
Haibach (10) Patent No.: US 10,493,227 B2
(45) Date of Patent: Dec. 3, 2019

(54) HEADGEAR TUBING ASSEMBLY AND INTEGRATED PRESSURE SENSING (71) Applicant: KONINKLIJKE PHILIPS N.V., Eindhoven (NL)

(72) Inventor: Richard Thomas Haibach, Verona, PA (US)

(73) Assignee: Koninklijke Philips N.V., Eindhoven (NL)

(*) Notice: Subject to any disclaimer, the term of this patent is extended or adjusted under 35 U.S.C. 154(b) by 560 days.

(21) Appl. No.: 15/119,543

(22) PCT Filed: Feb. 18, 2015

(86) PCT No.: PCT/IB2015/051216
§ 371 (c)(1),
(2) Date: Aug. 17, 2016

(87) PCT Pub. No.: WO2015/125080
PCT Pub. Date: Aug. 27, 2015

(65) Prior Publication Data
US 2017/0333658 A1 Nov. 23, 2017

Related U.S. Application Data (60) Provisional application No. 61/940,873, filed on Feb. 18, 2014.

(51) Int. Cl.
*A61M 16/06* (2006.01)
*A61M 16/08* (2006.01)
*A61M 16/00* (2006.01)

(52) U.S. Cl.
CPC .... *A61M 16/0611* (2014.02); *A61M 16/0666* (2013.01); *A61M 16/0683* (2013.01);
(Continued)

(58) Field of Classification Search
CPC ....... A61B 5/0836; A61B 5/085; A61B 5/087; A61B 5/097; A61B 5/411; A61B 5/6819;
(Continued)

(56) References Cited

U.S. PATENT DOCUMENTS

| 3,643,660 | A | * | 2/1972 | Hudson | A61M 16/0666 128/207.18 |
| 3,802,431 | A | * | 4/1974 | Farr | A61M 16/0666 128/207.18 |
| 4,989,599 | A | * | 2/1991 | Carter | A61M 16/0666 128/204.18 |
| 5,099,836 | A | * | 3/1992 | Rowland | A61M 16/0666 128/204.23 |
| 6,349,724 | B1 | * | 2/2002 | Burton | A61M 16/0057 128/204.18 |

(Continued)

FOREIGN PATENT DOCUMENTS

GB 2465358 A 5/2010
WO WO9011791 A1 10/1990
(Continued)

*Primary Examiner* — Annette Dixon
(74) *Attorney, Agent, or Firm* — Michael W. Haas (57) ABSTRACT A patient interface device includes a sealing cushion, and a tubing assembly structured to receive a breathing gas from a pressure generating device. The tubing assembly has: (i) a first chamber fluidly coupled to the sealing cushion, the first chamber being structured to deliver a flow of the breathing gas to the sealing cushion, and (ii) a second chamber having a pressure sensing module disposed therein, the second chamber having a closed end and an open end, the open end being fluidly coupled to the sealing cushion such that the second chamber is structured to carry only a positive pressure and substantially zero gas flow.

11 Claims, 4 Drawing Sheets (52) U.S. Cl.
CPC ..... *A61M 16/0875* (2013.01); *A61M 16/0816* (2013.01); *A61M 2016/0027* (2013.01); *A61M 2205/3331* (2013.01); *A61M 2205/3569* (2013.01); *A61M 2210/0618* (2013.01)

(58) Field of Classification Search
CPC .......... A61M 16/0057; A61M 16/0066; A61M 16/0069; A61M 16/024; A61M 16/06; A61M 16/0611; A61M 16/0666; A61M 16/0672; A61M 16/0677; A61M 16/0683; A61M 16/0816; A61M 16/085; A61M 16/0858; A61M 16/0875; A61M 16/12; A61M 16/125; A61M 16/202; A61M 2016/0021; A61M 2016/0027; A61M 2016/0036; A61M 2016/0039; A61M 2202/0007; A61M 2202/0208; A61M 2202/03; A61M 2205/3331; A61M 2205/3569; A61M 2210/0618; A61M 2210/0625; A61M 2230/005; A61M 2230/205; A61M 2230/432
See application file for complete search history.

(56) References Cited

U.S. PATENT DOCUMENTS

| | | | |
|---|---|---|---|
| 7,007,694 B2 * | 3/2006 | Aylsworth | A61M 16/0666 128/206.11 |
| 8,333,200 B2 | 12/2012 | Tero | |
| 2003/0094178 A1 * | 5/2003 | McAuley | A61M 16/0666 128/207.18 |
| 2009/0173350 A1 * | 7/2009 | Swanson | A61M 16/0666 128/207.18 |
| 2009/0299158 A1 | 12/2009 | Boatner | |
| 2011/0067704 A1 | 3/2011 | Kooij | |
| 2012/0052469 A1 | 3/2012 | Sobel | |
| 2012/0232420 A1 | 9/2012 | Salamitou | |
| 2013/0211275 A1 * | 8/2013 | Curti | A61M 16/0666 600/543 |

FOREIGN PATENT DOCUMENTS

| | | |
|---|---|---|
| WO | WO2012114004 A1 | 8/2012 |
| WO | WO2012156885 A1 | 11/2012 |
| WO | WO2013082650 A1 | 6/2013 |
| WO | WO2013148901 A1 | 10/2013 |

* cited by examiner

HEADGEAR TUBING ASSEMBLY AND INTEGRATED PRESSURE SENSING

CROSS-REFERENCE TO RELATED APPLICATIONS

This patent application claims the priority benefit under 35 U.S.C. § 371 of international patent application no. PCT/IB2015/051216, filed Feb. 18, 2015, which claims the priority benefit under 35 U.S.C. § 119(e) of U.S. Provisional Application No. 61/940,873 filed on Feb. 18, 2014, the contents of which are herein incorporated by reference.

BACKGROUND OF THE INVENTION

1. Field of the Invention

The present invention relates to respiratory patient interface devices, and, in particular, to a patient interface device having a headgear component that provides both an integrated flow path for delivery of breathing gas to the patient and a separate path for pressure sensing.

2. Description of the Related Art

There are numerous situations where it is necessary or desirable to deliver a flow of breathing gas non-invasively to the airway of a patient, i.e., without intubating the patient or surgically inserting a tracheal tube into the patient's esophagus. For example, it is known to ventilate a patient using a technique known as non-invasive ventilation. It is also known to deliver positive airway pressure (PAP) therapy to treat certain medical disorders, the most notable of which is obstructive sleep apnea (OSA). Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component having a soft, flexible sealing cushion on the face of a patient. The mask component may be, without limitation, a nasal mask that covers the patient's nose, a nasal cushion having nasal prongs that are received within the patient's nares, a nasal/oral mask that covers the patient's nose and mouth, or a full face mask that covers the patient's face. Such patient interface devices may also employ other patient contacting components, such as forehead supports, cheek pads and chin pads. The patient interface device is connected to a gas delivery tube or conduit and interfaces the ventilator or pressure support device with the airway of the patient so that a flow of breathing gas can be delivered from the pressure/flow generating device to the airway of the patient. It is known to maintain such devices on the face of a wearer by a headgear having one or more straps adapted to fit over/around the patient's head.

Some patient interface devices employ a small diameter pressure pick off hose coupled to the mask and a pressure sensor for measuring the pressure at the mask at any particular time. Knowing the pressure at the mask is useful enable the gas delivery system to account for varying pressure drops in the flexible gas delivery hose or hoses which deliver gas to the mask. For example, if the hose were to be partially collapsed during use (e.g., the patient lays on the hose), delivered pressure would be reduced and the pressure sensor at the mask will read low. In response, the gas delivery system can increase the generated pressure to compensate for the pressure decrease resulting from the collapse.

However, because current pressure pick off hoses have relatively small diameters (e.g., about 1-2 mm), they can be easily occluded by water droplets or other debris. Such occlusion adversely affects the ability of the associated pressure sensor to measure mask pressure accurately.

SUMMARY OF THE INVENTION

Accordingly, it is an object of the present invention to provide a patient interface device that overcomes the shortcomings of patient interface devices described above. In one embodiment, a patient interface device is provided that includes a sealing cushion, and a tubing assembly structured to receive a breathing gas from a pressure generating device. The tubing assembly has: (i) a first chamber fluidly coupled to the sealing cushion, the first chamber being structured to deliver a flow of the breathing gas to the sealing cushion, and (ii) a second chamber having a pressure sensing module disposed therein, the second chamber having a closed end and an open end, the open end being fluidly coupled to the sealing cushion such that the second chamber is structured to carry only the positive pressure and substantially zero gas flow.

In another embodiment, a method of operating a breathing gas delivery system having a patient interface device including a sealing cushion and a tubing assembly coupled to the sealing cushion is provided. The method includes generating a flow of breathing gas, providing the flow of breathing gas to the sealing cushion through a first chamber of the tubing assembly fluidly coupled to the sealing cushion, and providing only a positive pressure and substantially zero gas flow to a pressure sensing module provided within a second chamber of the tubing assembly, the second chamber having a closed end and an open end, the open end being fluidly coupled to the sealing cushion.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

As used herein, the term "substantially zero gas flow" shall mean a flow of less than 5 Standard Liters per Minute (SLPM) at a Pressure of 5 cm H2O. Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
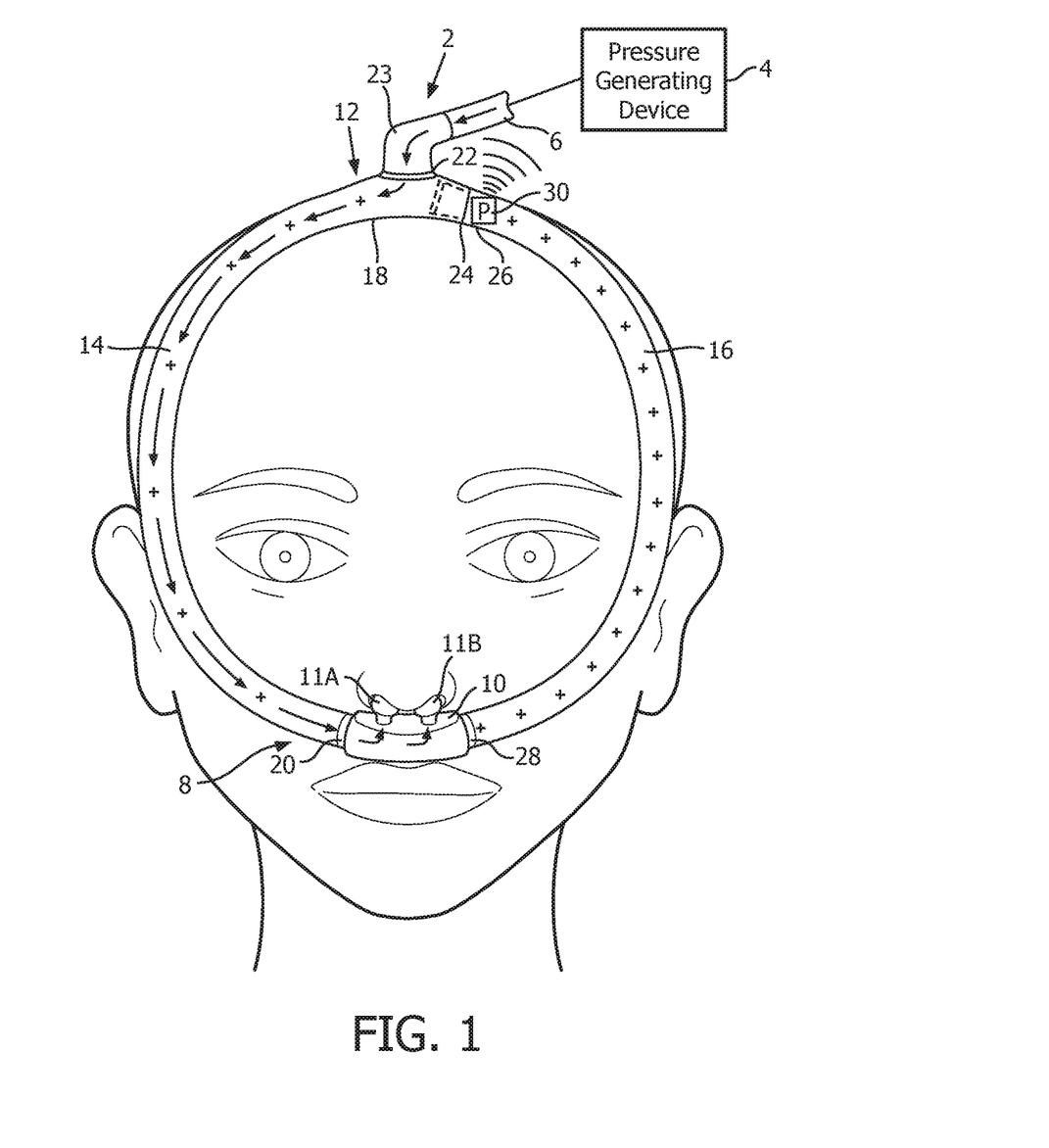
FIG. 1 is a schematic diagram of a system adapted to provide a regimen of respiratory therapy to a patient according to one exemplary embodiment of the invention.

A system 2 adapted to provide a regimen of respiratory therapy to a patient according to one exemplary embodiment of the invention is generally shown in FIG. 1. System 2 includes a pressure generating device 4, a delivery conduit 6, and a patient interface device 8. Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8.

In the exemplary embodiment, patient interface device 8 is a nasal cushion type patient interface having nasal prongs that are received within the nares of the patient (commonly referred to as a "pillows style" nasal cushion). However, other types of patient interface devices, such as, without limitation, a nasal mask type patient interface that covers the nose of a patient, a nasal saddle type patient interface structured to be placed against the lower, underside portion of the nose of a patient (wherein the patient's nares are engaged and covered), a nasal/oral mask type patient interface that covers the nose and mouth of a patient, or a full face mask type patient interface that covers the patient's face, which facilitate the delivery of the flow of breathing gas to, and the removal of a flow of exhalation gas from, the airway of such a patient may be used while remaining within the scope of the present invention.

In the illustrated embodiment, patient interface device 8 includes a pillows style sealing cushion 10 having nasal prongs 11A and 11B made of flexible, cushiony, elastomeric material, such as, without limitation, silicone, an appropriately soft thermoplastic elastomer, a closed cell foam, or any combination of such materials. Pillows style sealing cushion 10 is coupled to a tubing assembly 12. As described in detail below, tubing assembly 12 is asymmetric in structure and is configured such that a first side thereof carries and provides both a flow of breathing gas (indicated by the →symbols in FIG. 1) and positive pressure (indicated by the + symbols in FIG. 1) to one side of sealing cushion 10 while a second side thereof carries only positive static pressure (and zero gas flow) (indicated by the + symbols only in FIG. 1) to a pressure sensor. Because this configuration eliminates any gas flow from the path that includes the pressure sensor, it ensures optimal performance of the pressure sensor (by eliminating any pressure drop that may otherwise be introduced by a gas flow). This configuration also allows the use of a much larger conduit for carrying the static pressure to the pressure sensor, as compared to prior art pressure pick off tubes (e.g., widths or diameters of around 5 mm or larger). As a result, the path that includes the pressure sensor is less likely to be occluded by water droplets or other debris and is easier to clean.

In an alternative embodiment, rather than having the second side of tubing assembly 12 carry only positive static pressure (and zero gas flow), tubing assembly 12 may be structured such that the second side of tubing assembly 12 carries positive static pressure and a flow of less than 5 Standard Liters per Minute (SLPM) at a Pressure of 5 cm H2O. Such a flow would be low enough to ensure that the pressure drop that the second side of tubing assembly 12 experiences would be negligible.

As seen in FIG. 1, in the exemplary embodiment, tubing assembly 12 includes a first conduit member 14 structured to rest along a first side of the patient's head and a second conduit member 16 structured to rest along a second side of the patient's head when patient interface device 8 is donned by the patient. As such, in the exemplary embodiment, tubing assembly 12 forms part of a headgear component that secures patient interface device 8 to the head of the patient. In the illustrated embodiment, first conduit member 14 and second conduit member 16 are made of a rigid or semi-rigid material, such as, without limitation, an injection molded thermoplastic or silicone. Each of these components is described in greater detail below.

Figure 2:
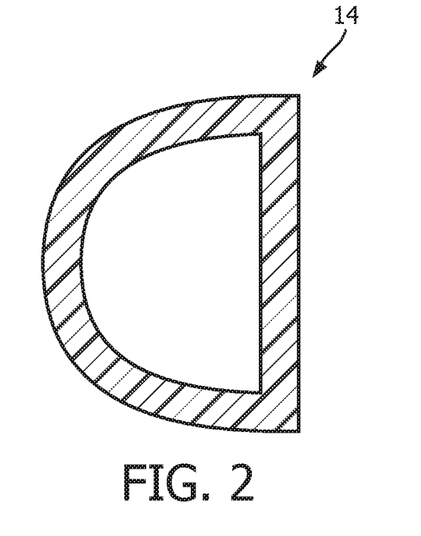
FIGS. 2 and 3 are cross-sectional diagrams of conduit members forming a part of a tubing assembly of the system of FIG. 1.

First conduit member 14 includes a first end 18 and a second, opposite end 20. First end 18 includes an opening 22 sized to sealingly receive and hold a coupling connector 23 that in turn is coupled to a distal end of delivery conduit 6. First end 18 also includes an opening 24 sized to sealingly receive and hold a first end 26 of second conduit member 16 (described below). Second end 20 of first conduit member 14 is open and is removeably and fluidly coupled to a first side of sealing cushion 10. In addition, first conduit member 14 has a hollow cross-sectional shape as shown in FIG. 2. As a result, first conduit member 14 is structured to receive both a flow of breathing gas and positive pressure from delivery conduit 6 (generated by pressure generating device 4) and provide that flow and positive pressure to sealing cushion 10 for delivery to the airways of the patient through nasal prongs 11A and 11B.

Figure 3:
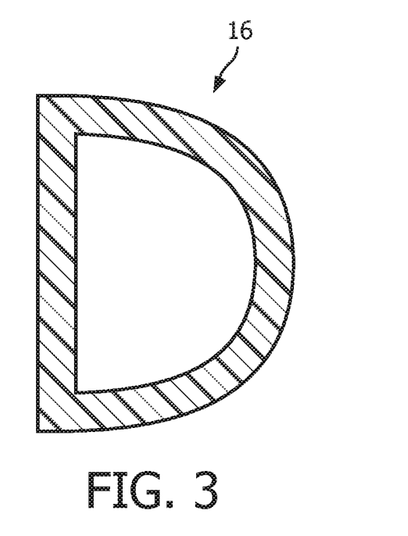

Second conduit member 16 includes a first end 26 and a second, opposite end 28. First end 26 is closed/sealed while second end 28 is open. The significance of this feature is described in greater detail herein. As noted above, first (closed/sealed) end 26 is sealingly received and held within opening 24 of first end 18 of first conduit member. Second (open) end 20 of first conduit member 14 is removeably and fluidly coupled to the second (opposite) side of sealing cushion 10. In addition, like first conduit member 14, second conduit member 16 has a hollow cross-sectional shape as shown in FIG. 3. One or more straps (not shown) forming part of the headgear component are attached to first conduit member 14 and second conduit member 16 to help in securing patient interface device 8 to the patient's head.

Furthermore, as seen in FIG. 1, a pressure sensing module 30 is provided and mounted within the interior chamber of second conduit member 16. Pressure sensing module 30 is structured to determine the static pressure within second conduit member at any time and wirelessly communicate that static pressure to pressure generating device 4. For that purpose, pressure sensing module 30 includes a pressure transducer element and a wireless transmitting element. The pressure transducer element may be any type of suitable pressure transducer, such as, without limitation, a transducer based on piezoresistive strain gauge, capacitive, electromagnetic, piezoelectric, optical, or potentiometric technology. The wireless transmitting element may be based on any type of suitable wireless communications technology, such as, without limitation, Bluetooth® technology. Alternatively, pressure sensing module 30 may be structured to communicate measured static pressure information to pressure generating device 4 in a wired fashion.

In operation, the patient dons patient interface device 8 as shown in FIG. 1 and pressure generating device 4 generates a flow of positive pressure breathing gas. The flow of positive pressure breathing gas is delivered to tubing assembly 12 by delivery conduit 6. At tubing assembly 12, both the flow of breathing gas (indicated by the →symbols in FIG. 1) and the positive pressure (indicated by the + symbols in FIG. 1) will be carried by first conduit member 14 to one side of sealing cushion 10. At sealing cushion 10, the flow and positive pressure are delivered to nasal prongs 11A and 11B, and then to the airways of the patient.

However, because the first end 26 of second conduit member 16 is closed/sealed, gas flow will not be able to enter second conduit member 16. Instead, only positive static pressure (and zero gas flow) (indicated by the + symbols only in FIG. 1) will enter and be passed within second conduit member 16. That positive static pressure is provided to pressure sensing module 30. Pressure sensing module 30 measures the static pressure and transmits a signal to pressure generating device 4 that indicates the measured pressure level. In response, pressure generating device 4 may then make any adjustments that are deemed necessary to the generated pressure (e.g., to account for any pressure drops in delivery conduit 6 or first conduit member 14). In an alternative embodiment, rather than having second conduit member 16 carry only positive static pressure (and zero gas flow), second conduit member 16 may be structured such that it carries positive static pressure and a flow of less than 5 Standard Liters per Minute (SLPM) at a Pressure of 5 cmH2O. Such a flow would be low enough to ensure that the pressure drop that second conduit member 16 experiences would be negligible.

Figure 4:
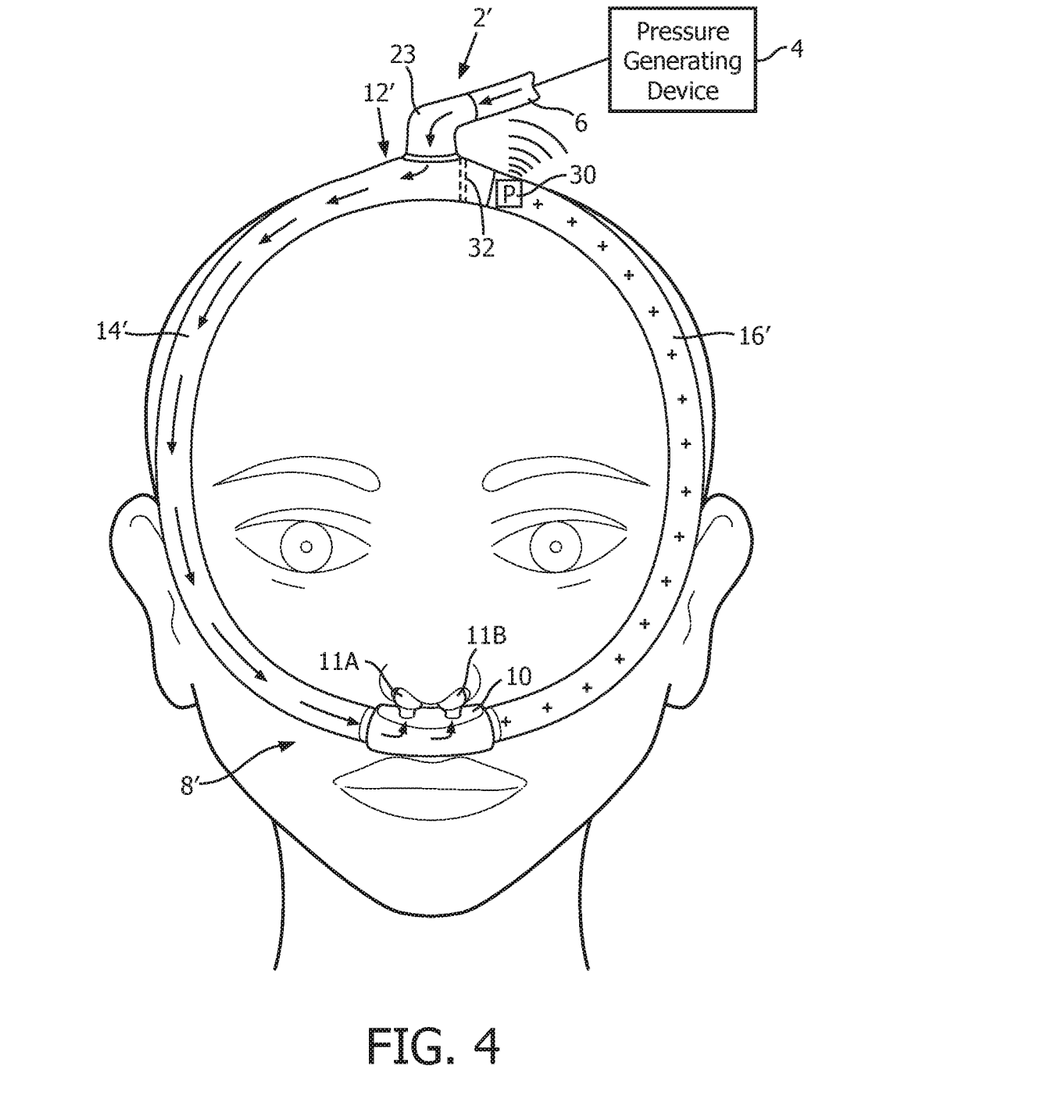
FIG. 4 is a schematic diagram of a system adapted to provide a regimen of respiratory therapy to a patient according to an alternative exemplary embodiment of the invention.

In system 2 according to the exemplary embodiment as just described, first conduct member 14 and second conduit member 16 of tubing assembly 12 are separated components that are coupled together as described to form tubing assembly 12. FIG. 4 shows a system 2' according to an alternative exemplary embodiment that includes an alternative tubing assembly 12'. As seen in FIG. 4, tubing assembly 12' is formed as a single, integrated piece (e.g., by molding) including first conduit member 14' and second conduit member 16'. In this configuration, the first end of second conduit member 16' is provided with a divider wall 32 that completely separates first conduit member 14' and second conduit member 16' and closes/seals that end of second conduit member 16'. As a result, only static pressure and zero flow are able to enter second conduit member 16'. Thus, the operation of system 2' as just described is substantially identical to the operation of system 2. In an alternative embodiment, rather than having second conduit member 16' carry only positive static pressure (and zero gas flow), second conduit member 16' may be structured such that it carries positive static pressure and a flow of less than 5 Standard Liters per Minute (SLPM) at a Pressure of 5 cm H2O. Such a flow would be low enough to ensure that the pressure drop that second conduit member 16' experiences would be negligible.

Figure 5:
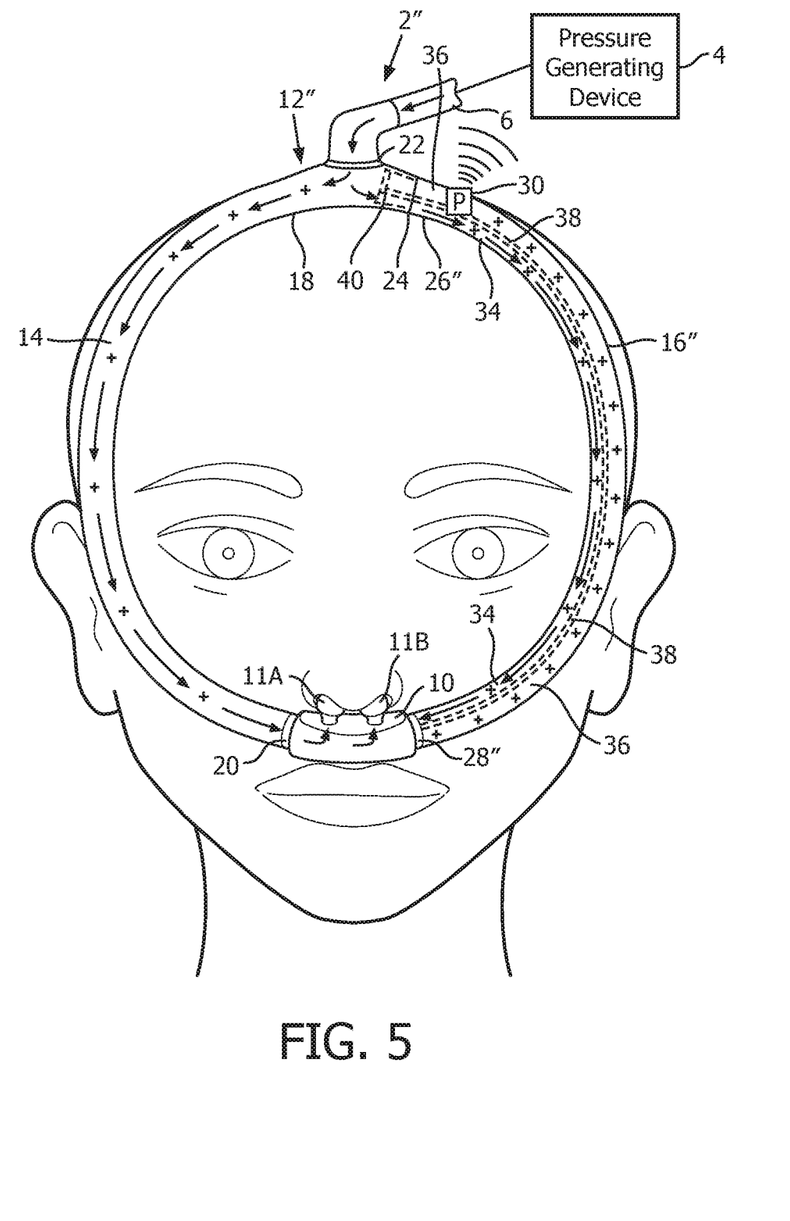
FIG. 5 is a schematic diagram of a system adapted to provide a regimen of respiratory therapy to a patient according to a further alternative exemplary embodiment of the invention.

A system 2" adapted to provide a regimen of respiratory therapy to a patient according to another alternative exemplary embodiment of the invention is generally shown in FIG. 5. System 2" is similar to system 2 and includes a pressure generating device 4 and a delivery conduit 6 as described herein. System 2", however, includes an alternative patient interface device 8".

Figure 6:
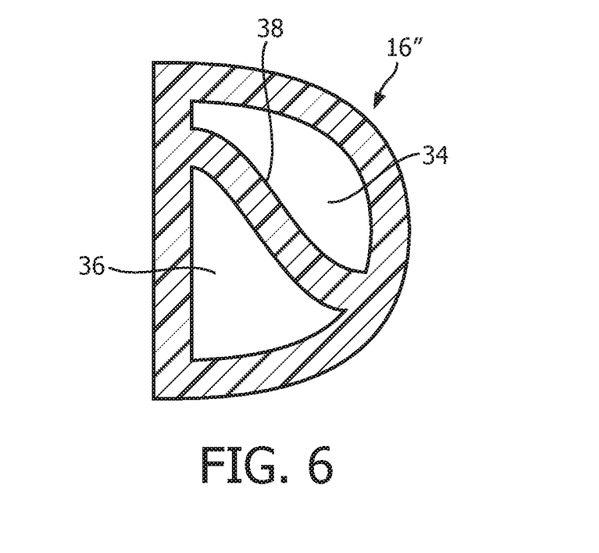
FIG. 6 is a cross-sectional diagram of a conduit member forming a part of a tubing assembly of the system of FIG. 5.

As seen in FIG. 5, alternative patient interface device 8" includes an asymmetric tubing assembly 12". Tubing assembly 12" includes a first conduit member 14 as described herein. Tubing assembly 12" also includes an alternative second conduit member 16" structured to rest along the second side of the patient's head when patient interface device 8" is donned by the patient. Second conduit member 16" includes a first end 26" received and held within opening 24 of first conduit member 14 and a second end 28" releasably fluidly coupled to the second end of sealing cushion 10. In addition, referring to FIG. 6, which is a cross-section view of second conduit member 16", second conduit member 16" is divided into first and second internal chambers 34, 36 by internal wall 38 that runs along the entire length of second conduit member 16". At the second end 28" of second conduit member 16", both the first internal chamber 34 and the second internal chamber 36 are open and in fluid communication with the interior of sealing cushion 10. However, at the first end 26" of second conduit member 16", only the first internal chamber 34 is open and in fluid communication with the interior of first conduit member 14. In contrast, at the first end 26" of second conduit member 16", second internal chamber 36 is closed/sealed by wall 40. As such, in system 2", first conduit member 14 and first internal chamber 34 are both structured to carry both the flow of breathing gas (indicated by the →symbols in FIG. 5) and positive pressure (indicated by the + symbols in FIG. 5) to each side of sealing cushion 10, second internal chamber 36 is structured to carry only positive static pressure (and zero gas flow) (indicated by the + symbols only in FIG. 5) to pressure sensing module 30.

In operation, the patient dons patient interface device 8" as shown in FIG. 5 and pressure generating device 4 generates a flow of positive pressure breathing gas. The flow of positive pressure breathing gas is delivered to tubing assembly 12" by delivery conduit 6. At tubing assembly 12", both the flow of breathing gas (indicated by the →symbols in FIG. 5) and the positive pressure (indicated by the + symbols in FIG. 5) will be carried by first conduit member 14 and first internal chamber 34 to sealing cushion 10 (opposite sides thereof). At sealing cushion 10, the flow and positive pressure are delivered to nasal prongs 11A and 11B, and then to the airways of the patient. However, since the first end of second internal chamber 36 is closed/sealed, gas flow will not be able to enter second internal chamber 36. Instead, only positive static pressure (and zero gas flow) (indicated by the + symbols only in FIG. 5) will enter and be passed within second internal chamber 36 That positive static pressure is provided to pressure sensing module 30.

Pressure sensing module 30 measures the static pressure and transmits a signal to pressure generating device 4 that indicates the measured pressure level. In response, pressure generating device 4 may then make any adjustments that are deemed necessary to the generated pressure (e.g., to account for any pressure drops in system 2"). In an alternative embodiment, rather than having second internal chamber 36 carry only positive static pressure (and zero gas flow), second internal chamber 36 may be structured such that it carries positive static pressure and a flow of less than 5 Standard Liters per Minute (SLPM) at a Pressure of 5 cm H2O. Such a flow would be low enough to ensure that the pressure drop that second internal chamber 36 experiences would be negligible.

In a further alternative embodiment, tubing assembly 12" may be formed as a single, integrated piece (e.g., by molding) including first conduit member 14 and second conduit member 16". In this configuration, the first end of second conduit member 16" is provided with a divider wall that completely separates first conduit member 14 and second internal chamber 36 and closes/seals that end of second internal chamber 36.

While the present invention illustrates second conduit members 16, 16' as having a generally tubular configuration, it is to be understood that other shapes, sizes, geometries, and configurations are contemplated by the present invention. For example, second conduits 16, 16' need not be a mirror image of the conduit provided on the other side of the head. Instead, it can have bulbous areas, curves, and other configurations so long as it provides an area of dead space for mounting a sensor distal from the sealing element. In addition, the present invention contemplates that either of second conduits 16, 16' need not be disposed on the head of the user. Instead, it can dangle off of the head so long as it is in fluid communication with the airway of the user.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device, comprising:
a sealing cushion; and
a tubing assembly structured to receive a flow of breathing gas from a pressure generating device, the tubing assembly having: (i) a first chamber fluidly coupled to the sealing cushion, the first chamber being structured to deliver a flow of the breathing gas to the sealing cushion, and (ii) a second chamber having a pressure sensing module disposed inside the second chamber, the second chamber having a closed end and an open end, the open end being fluidly coupled to the first chamber via the sealing cushion such that the second chamber is structured to have a positive pressure and substantially zero gas flow therein responsive to the flow of breathing gas being provided to the first chamber, wherein the first chamber is formed in a first conduit member structured to rest along a first side of a patient's head when the patient interface device is donned by the patient, and wherein the second chamber is formed in a second conduit member structured to rest along a second side of the patient's head when the patient interface device is donned by the patient, and wherein the first conduit member has a first end and a second end, the second end being fluidly coupled to the sealing cushion, the first end having a first opening structured to receive the breathing gas and a second opening receiving the closed end of the second chamber.

2. The patient interface device according to claim 1, wherein the second conduit member has a third chamber formed therein adjacent the second chamber, the third chamber having a first open end adjacent the closed end of the second chamber and received within the second opening of the first conduit member and a second open end fluidly coupled to the sealing cushion such that the third chamber is structured to carry the positive pressure and gas flow.

3. The patient interface device according to claim 2, wherein the second conduit member has an internal wall that runs along an entire length of second conduit member and defines the second chamber and the third chamber.

4. The patient interface device according to claim 1, wherein the pressure sensing module is a wireless pressure sensing module having a pressure transducer element and a wireless transmitting element.

5. The patient interface device according to claim 1, wherein the second chamber is structured to carry only the positive pressure and zero gas flow.

6. A patient interface device comprising:
a sealing cushion; and
a tubing assembly structured to receive a flow of breathing gas from a pressure generating device, the tubing assembly having: (i) a first chamber fluidly coupled to the sealing cushion, the first chamber being structured to deliver a flow of the breathing gas to the sealing cushion, and (ii) a second chamber having a pressure sensing module disposed inside the second chamber, the second chamber having a closed end and an open end, the open end being fluidly coupled to the first chamber via the sealing cushion such that the second chamber is structured to have a positive pressure and substantially zero gas flow therein responsive to the flow of breathing gas being provided to the first chamber, wherein the first chamber is formed in a first conduit member structured to rest along a first side of a patient's head when the patient interface device is donned by the patient, and wherein the second chamber is formed in a second conduit member structured to rest along a second side of the patient's head when the patient interface device is donned by the patient, wherein the tubing assembly is integrally formed from the first conduit member and the second conduit member, wherein the first conduit member has a first end and a second end, the second end being fluidly coupled to the sealing cushion, the first end having a first opening structured to receive the breathing gas and a divider wall separating the first conduit member and the second conduit member and forming the closed end of the second chamber.

7. A method of operating a breathing gas delivery system having a patient interface device including a sealing cushion and a tubing assembly coupled to the sealing cushion, the method comprising:
generating a flow of breathing gas;
providing the flow of breathing gas to the sealing cushion through a first chamber of the tubing assembly fluidly coupled to the sealing cushion; and
responsive to providing the flow of breathing gas to the sealing cushion through the first chamber, providing a positive pressure and substantially zero gas flow to a pressure sensing module provided inside a second chamber of the tubing assembly, the second chamber having a closed end and an open end, the open end being fluidly coupled to the first chamber via the sealing cushion, wherein the first chamber is formed in a first conduit member structured to rest along a first side of a patient's head when the patient interface device is donned by the patient, and wherein the second chamber is formed in a second conduit member structured to rest along a second side of the patient's head when the patient interface device is donned by the patient, and wherein the first conduit member has a first end and a second end, the second end being fluidly coupled to the sealing cushion, the first end having a first opening structured to receive the flow of breathing gas and a second opening receiving the closed end of the second chamber.

8. The method according to claim 7, wherein the second conduit member has a third chamber formed therein adjacent the second chamber, the third chamber having a first open end adjacent the closed end of the second chamber and received within the second opening of the first conduit member and a second open end fluidly coupled to the sealing cushion such that the third chamber is structured to carry the positive pressure and gas flow.

9. The method according to claim 8, wherein the second conduit member has an internal wall that runs along an entire length of second conduit member and defines the second chamber and the third chamber.

10. The method according to claim 7, further comprising measuring the positive pressure using the pressure sensing module to generate a measured pressure level and wirelessly communicating the measured pressure level to a pressure generating device used to generate the flow of breathing gas.

11. The method according to claim 7, comprising providing only the positive pressure and zero gas flow to a pressure sensing module provided within a second chamber of the tubing assembly.

* * * * *